United States Patent [19]
Laufenberg et al.

[11] Patent Number: 5,481,025
[45] Date of Patent: Jan. 2, 1996

[54] SATURATED BRANCHED FATTY ACIDS CONTAINING 20 TO 28 CARBON ATOMS OR ESTERS THEREOF WITH $C_{1-36}$ ALKANOLS, A PROCESS FOR THEIR PRODUCTION AND THEIR USE

[75] Inventors: Alfred Laufenberg, Dormagen; Arno Behr, Duesseldorf, both of Germany

[73] Assignee: Henkel Kommanditgesellschaft auf Aktien TFP/Patentabteilung, Duesseldorf, Germany

[21] Appl. No.: 915,845

[22] PCT Filed: Jan. 15, 1991

[86] PCT No.: PCT/EP91/00053

§ 371 Date: Jul. 24, 1992

§ 102(e) Date: Jul. 24, 1992

[87] PCT Pub. No.: WO91/11426

PCT Pub. Date: Aug. 8, 1991

[30] Foreign Application Priority Data

Jan. 24, 1990 [DE] Germany ............ 40 02 011.8

[51] Int. Cl.⁶ .................................................. C11C 3/12
[52] U.S. Cl. ............................................. 554/142; 554/141
[58] Field of Search .................................... 554/141, 142, 554/174, 163, 165, 162; 252/562

[56] References Cited

U.S. PATENT DOCUMENTS

| | | | |
|---|---|---|---|
| 3,636,122 | 1/1972 | Cramer et al. | 260/680 |
| 3,734,859 | 5/1973 | Ward | 252/108 |
| 3,753,968 | 8/1973 | Ward | 260/97.6 |
| 4,371,469 | 2/1983 | Foglia et al. | 554/161 |
| 4,973,431 | 11/1990 | Struve et al. | 554/141 |

FOREIGN PATENT DOCUMENTS

| | | |
|---|---|---|
| 10807 | 1/1983 | European Pat. Off. . |
| 0010807 | 10/1989 | European Pat. Off. . |
| 2202727 | 5/1974 | France . |
| 2016133 | 12/1970 | Germany . |
| 2253930 | 5/1974 | Germany . |
| 8400884 | 3/1984 | WIPO . |

OTHER PUBLICATIONS

Radical Addition Of Methyl Acetoxy Acetate To Olefins And Pyrolysis of the Adducts Yu. N. Ogibin et al Feb. 1967. CA66:10623: 1966.
Cas 105:66269, 1986 m=40596–46–1D.
Fat. Sci. Tech., 1,1, 1988, pp. 1–5.
Fat. Sci. Tech., 1, 1989, pp. 18–23.
Biomed. Mass Spectrom, A. Smith et al., pp. 347–349 1979.
Journal of Molecular Catalysis, 22, 1984, pp. 363–365.
Comprehensive Organometallic Chem., G. Wilkinson (ed.), pp. 414–429 1982.

*Primary Examiner*—José G. Dees
*Assistant Examiner*—Samuel Barts
*Attorney, Agent, or Firm*—Wayne C. Jaeschke; John E. Drach; Henry E. Millson, Jr.

[57] ABSTRACT

Saturated, branched $C_{20-28}$ fatty acids or esters thereof esterified with $C_{1-36}$ alkanols produced by the process comprising: (a) reacting unsaturated fatty acids containing 18 to 22 carbon atoms and more than one olefinic bond or esters thereof esterified with $C_{1-36}$ alkanols with ethylene at a temperature of from about 50° C. to about 140° C. and at a pressure of from about 5 to about 60 bar in the presence of transition metal compounds selected from the group consisting of Ru, Rh, Pd, Ir, or Pt wherein the molar ratio of ethylene to fatty acid or fatty acid ester is from about 1:1 to about 3:1 to form an olefinically unsaturated adduct and, (2) hydrogenating said adduct in the presence of a hydrogenation catalyst at a temperature of from about 70° C. to about 120° C. and under a hydrogen pressure of from 10 to about 30 bar.

The invention also relates to the process for producing the saturated acids or esters, and to a process for depressing the pour point of a lubricant and to the lubricant so produced.

2 Claims, No Drawings

SATURATED BRANCHED FATTY ACIDS CONTAINING 20 TO 28 CARBON ATOMS OR ESTERS THEREOF WITH $C_{1-36}$ ALKANOLS, A PROCESS FOR THEIR PRODUCTION AND THEIR USE

BACKGROUND OF THE INVENTION

1. Field of the Invention

This invention relates to saturated branched fatty acids or esters thereof with $C_{1-36}$ alkanols obtainable by hydrogenation of olefinically unsaturated adducts of ethylene with polyunsaturated $C_{18-22}$ fatty acids or esters thereof with $C_{1-36}$ alkanols in molar ratios of ethylene to fatty acids or fatty acid esters of 1:1 to 3:1.

2. Statement of Related Art

Fatty acids branched in the alkyl chain of the Guerbet acid type, obtainable by "guerbetization" of the corresponding fatty alcohols and oxidation of the Guerbet alcohols to the corresponding acids, are technologically interesting intermediate products because they, or their alkyl esters, have distinctly reduced pour points by comparison with the corresponding unbranched isomers. However, the production of Guerbet acids is technologically complicated and can only be carried out with unsatisfactory yields. Accordingly, there has been no shortage of attempts to produce corresponding fatty acid derivatives branched in the alkyl chain from fatty acids or esters thereof. A typical example of this is the layer-silicate-catalyzed dimerization of fatty acids. Unfortunately, considerable quantities of trimeric fatty acids and methyl-branched fatty acids, so-called isofatty acids, are also formed in this reaction. Another, albeit complicated, process gives branched fatty acid derivatives from conjuene fatty acids in the trans-trans form with activated dienophiles under the conditions of a Dieis-Alder reaction; for example, a branched $C_{21}$ dicarboxylic acid can be obtained in this way from linoleic acid and acrylic acid, cf. U.S. Pat. No. 3,734,859, 3,753,968, DE-B 2 253 930. Other branched fatty acid derivatives have been obtained by thermal or acid-catalyzed addition of activated enophiles onto unsaturated fatty acid derivatives. For example, maleic anhydride can be added onto oleic acid in the presence of an acid as catalyst in yields of up to 70%, cf. Fat. Sci. Technol., 1, 1 (1988). However, the presence of more than one carboxyl group in the reaction products mentioned above has often proved to be troublesome.

Finally, attempts have also been made to add saturated hydrocarbons onto fatty acids by heat-initiated radical addition of saturated hydrocarbons onto fatty acids. The addition of cyclohexane onto oleic acid methyl ester at 340° C./200 bar gives alkyl-branched fatty acids with 70% selectivity, but in a yield of only 2.8%, of. J. O. Metzger et al., Fat. Sci. Technol. 1 (1989), 18.

DESCRIPTION OF THE INVENTION

The present invention is directed to the provision of saturated branched fatty acids or esters of the type mentioned at the beginning which can be readily obtained in high yields. The compounds provided in accordance with the invention are new products which, for example, differ in their chain length alone from the naturally occurring ethyl-branched fatty acids containing a total of 12 to 18 carbon atoms described in A. Smith et al. *Biomed. Mass Spectrom.*, 6 (8), 347–349.

The saturated branched fatty acids according to the invention or esters thereof may be obtained by hydrogenation of olefinically unsaturated adducts of ethylene with polyunsaturated $C_{18-12}$ fatty acids or esters thereof with $C_{1-36}$ alkanols in molar ratios of ethylene to fatty acids or fatty acid esters of 1:1 to 3:1.

These ethylene adducts are the subject of Applicants' patent application Ser. No. 07/915,696 (D 8752 PCT/US) filed at the same time as the present application to which reference is hereby specifically made and of which the essential disclosure is summarized in the following.

Suitable starting products for the production of the olefinically unsaturated adducts according to the cited patent application are unsaturated fatty acids containing 18 to 22 carbon atoms and more than one olefinic double bond, such as linoleic acid, isomerized linoleic acid containing conjugated double bonds (so-called $C_{18}$: 2-conjuene fatty acid), linolenic acid, arachidonic acid, docosadienoic acid, docosahexaenoic and eicosapentaenoic acid, which can be obtained in the form of technical mixtures with other fatty acids from renewable natural raw materials, for example from sunflower oil, tall oil or fish oil. As usual in oleochemistry, these polyunsaturated fatty acids are generally not used in the form of their pure compounds, but rather in the form of technical mixtures for the preparation of the adducts according to the invention. The above-mentioned fatty acids are preferably used not only as such, but also in the form of their esters with $C_{1-36}$ alkanols, more particularly with $C_{1-4}$ alkanols. Typical examples of such alkanols for the formation of esters with the fatty acids mentioned above are methanol, ethanol, propanol, butanol, pentanol, hexanol, octanol, decanol, dodecanol, tetradecanol, hexadecanol, octadecanol and higher fatty alcohols or fatty alcohol derivatives containing up to 36 carbon atoms, for example $C_{36}$ Guerbet alcohols.

According to the cited patent application, the polyunsaturated fatty acids or fatty acid esters mentioned above are added onto ethylene at elevated temperature and pressure in the presence of compounds of transition metals from the group consisting of Ru, Rh, Pd, Ir and Pt.

The following are typical examples of suitable catalysts:
$RhCl_3.3H_2O$
$RhBr_3.3H_2O$
$[(C_2H_4)_2RhCl]_2$
$Rh(NO_3)_3.2H_2O$
$Rh(OOCCH_3)_2.2H_2O$
$Rh(acetylacetonate)_3$
$RhF_3.6H_2O$
$RhI_3$
$Rh(CN)_3.3H_2O$
$Rh_2(SO_4)_3$
$Rh_2(CO_3)_3$
$[(1.5-cyclooctadiene)RhCl]_2$
$[(C_2H_4)_2Rh(acetylacetonate)$
$[(1.3-butadiene)RhCl]_2$
cyclopentadienyl-olefin complexes, such as $[(n-C_5H_5)Rh-(C_2H_4)_2]$.

Where the catalysts are present in anhydrous form, it may be advisable to add a small quantity of water to the reaction mixture.

The catalysts suitable for use in accordance with the cited patent application are known as such for the addition of ethylene onto alkadienes, cf. U.S. Pat. No. 3,636,122; M. Bochmann et al., Journal of Molecular Catalysis, 22 (1984), 363–365; G. Wilkinson (Ed.), Comprehensive Organometallic Chemistry, pages 414–429, Pergamon Press (1982); A.C.L. Su, Advances in Organometallic Chemistry, Vol. 17, pages 271–283. However, these publications, to the subject matter of which reference is hereby specifically made, are not concerned with the addition of alkenes onto fatty acids or fatty acid derivatives or other fatty compounds.

Other catalysts suitable for use in accordance with the cited patent application are, for example, $PdCl_2$
$PtCl_2$
$IrCl_3$
$OsCl_3$
$Ru(acetylacetonate)_3$.

Mixtures of 1:1, 2:1 and 3:1 adducts of ethylene with the fatty acids or fatty acid esters are generally formed with the catalysts mentioned above. However, the percentage contents of the various adducts can be varied by modifying the reaction conditions, such as pressure, temperature and reaction time. However, if suitable phosphine or phosphite ligands, for example $P(C_4H_9)_3$
$P(OC_4H_9)_3$
$P(C_6H_5)_3$
$P(OC_6H_5)_3$ or other ligands known from the prior art just discussed and from DE-B 20 16 133, are added to the reaction mixture in addition to the catalysts, the composition of the adduct mixtures may be selectively influenced. Thus, in the case of reaction systems which mainly give 2:1 adducts without such ligands, 3:1 adducts are mainly formed where large ligands are used while 1:1 adducts are mainly formed where small ligands are used. Similar effects can be obtained to an extent by addition to the reaction system of promoters such as $LiCl$, $FeCl_3$ or $AgBF_4$ which are also known as such from the last-mentioned prior art.

The structure of the olefinically unsaturated adducts described in the cited patent application is not uniform. In the case of linoleic acid (or the $C_{18}$ conjuene fatty acid derived therefrom), it could be shown that the addition of the first ethylene molecule takes place between the 9 and 12 positions of the carbon chain of the linoleic acid, the 1:1 adduct having the same number of double bonds as the fatty acid used as starting material. However, the position of the double bonds is uncertain. In no case are the double bonds further than 4 carbon atoms from the branching and, basically, they are in the α,δ- or α,γ-position to one another. The second and, optionally, the third ethylene molecule is then added onto a double bond situated in the branching. It may be assumed that at least some of the adducts obtained in accordance with the invention have one of the structures shown below; analogous carbon chains are present in the saturated compounds obtained in accordance with the present invention.

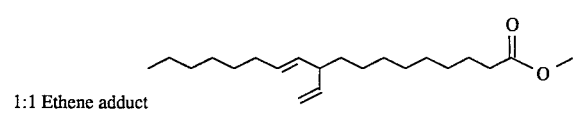

1:1 Ethene adduct

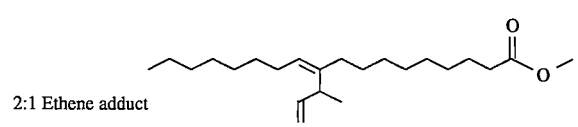

2:1 Ethene adduct

-continued

3:1 Ethene adduct

In one embodiment of the cited patent application, the polyunsaturated fatty acids optionally used in the form of their esters contain 2 to 5 and, more particularly, from 2 to 3 olefinic double bonds.

In another embodiment of the cited patent application, the adducts are obtained under an ethylene pressure in the range from 5 to 60 bar and at a temperature in the range from 50° to 140° C., the reaction optionally being carried out in the presence of inert organic solvents, such as hexane, chloroform or the like.

In another embodiment of the cited patent application, the catalysts are used in a quantity of 0.02 to 2 mol-%, based on fatty acids or fatty acid esters.

According to the cited patent application, rhodium compounds are advantageously used as the catalysts, rhodium compounds from the group consisting of $RhCl_3$ and $RhBr_3$ (including hydrates thereof) and $[(C_2H_4)_2RhCl]_2$ preferably being used as catalysts.

The saturated branched fatty acids or esters thereof with $C_{1-36}$ alkanols can be obtained by hydrogenation of the above-described starting products in accordance with the cited patent application. Suitable catalysts are the catalyst systems typically used in the hydrogenation of fats, such as Raney nickel, palladium/carbon catalysts and the like. The hydrogenation is preferably carried out at elevated temperature and pressure in the presence of the hydrogenation catalysts and, more preferably, at a temperature of 70° to 120° C. and under a hydrogen pressure of 10 to 30 bar.

The invention also relates to a process for the production of saturated branched fatty acids or esters having the features described above.

Finally, the invention relates to the use of the saturated branched fatty acids or esters thereof as lubricant additives and more particularly as pour point depressants.

The invention is illustrated by the following Examples.

The preparation of the starting compounds for the compounds according to the invention in accordance with the patent application cited above will first be described under nos. 1 to 13.

No. 1

8.2 g of a technical fatty acid mixture containing 56% by weight conjugated $C_{18}$:2 fatty acid were reacted with 100 mg $RhCl_3.3H_2O$ in 10 ml hexane for 20 h at 100° C./30 bar cold ethylene pressure in a 75 ml steel autoclave. 63.1% ethylene adducts, based on conjuene fatty acid, were obtained (as determined by gas chromatography), being made up of 34.9% 1:1 adduct, 44.2% 2:1 adduct and 20.9% 3:1 adduct.

No. 2

2.5 kg of a technical conjuene fatty acid according to Example 1, 0.8 g $RhCl_3.3H_2O$ and 1l hexane were reacted for 20 h at 100° C./20 bar constant ethylene pressure in a 5 liter stirred autoclave equipped with a turbine stirrer. Ethylene adducts were obtained in a yield of 89.4%, being made up of 23.7% 1:1 adduct, 41.7% 2:1 adduct and 34.6% 3:1 adduct.

No. 3

8.2 g of a technical linoleic acid methyl ester (67.8% methyl linoleate, 22.4% methyl oleate) and 100 mg $RhCl_3.3H_2O$ were reacted with 10 ml chloroform at 100° C. under a cold ethylene pressure of 20 bar. The adduct yield, based on methyl linoleate, was 57.8%, the adducts being made up of 30.8% 1:1 adduct, 42.0% 2:1 adduct and 27.2% 3:1 adduct.

No. 4

The repetition of Example 3 under a cold ethylene pressure of 30 bar produced an adduct yield of 57.6%, the adducts being made up of 31.5% 1:1 adduct, 52.2% 2:2 adduct and 16.3% 3:1 adduct.

No. 5

8.2 g of a technical $C_{18}$:2 conjuene methyl ester (containing 60.3% conjuene ester, 6.2% linoleic acid methyl ester and 24.4% oleic acid methyl ester) in 10 ml chloroform were reacted at 100° C./20 bar cold ethylene pressure. Ethylene adducts were obtained in a yield of 93.5%, the adducts being made up of 27.5% 1:1 adduct, 51.1% 2:1 adduct and 21.4% 3:1 adduct.

No. 6

The repetition of method 5 under a cold ethylene pressure of 30 bar produced a total yield of ethylene adducts of 88.5%, the adducts being made up of 36.5% 1:1 adduct, 51.0% 2:1 adduct and 12.1% 3:1 adduct.

No. 7

The repetition of method 6 in the presence of 185.1 mg $FeCl_3$ as promoter produced a total adduct yield of 81.8%, the adducts being made up of 22.8% 1:1 adduct, 46.9% 2:1 adduct and 30.3% 3:1 adduct.

No. 8

The repetition of method 6 with hexane instead of chloroform produced a total adduct yield of 87.4%, the adducts being made up of 24.8% 1:1 adduct, 59.7% 2:1 adduct and 15.5% 3:1 adduct.

No. 9

The repetition of method 6 with 74 mg $[(C_2H_5)_2RhCl]_2$ instead of $RhCl_3.3H_2O$ produced a total adduct yield of 78.0%, the adducts being made up of 24.2% 1:1 adduct, 61.8% 2:1 adduct and 13.0% 3:1 adduct. The total yield rose to 86.5% when 86.4 mg $P(C_4H_9)_3$ was added to the reaction mixture.

No. 10

The repetition of method 6 using 13 mg $RhBr_3.3H_2O$ instead of $RhCl_3.3H_2O$ in the absence of a solvent produced a total yield of ethylene adducts, based on the conjuene ester content, of 94.6%, the adducts being made up of 17.7% 1:1 adduct, 62.8% 2:1 adduct and 16.5% 3:1 adduct.

No. 11

Influence of phosphine and phosphite ligands

Method 3 was repeated with addition of 76.76 g (0.380 mmol) $P(C_4H_9)_3$. The total adduct yield was 54.5%, based on methyl linoleate, the adducts being made up of 32.4% 1:1 adduct, 16.2% 2:1 adduct and 6.0% 3:1 adduct.

Repetition with 9.50 mg (0.038 mmol) $P(OC_4H_9)_3$ produced a total adduct yield of 57.8%, the adducts being made up of 34.9% 1:1 adduct, 16.4% 2:1 adduct and 6.5% 3:1 adduct.

Repetition with 9.96 mg (0.038 mmol) $P(C_6H_5)_3$ produced a total adduct yield of 64.2%, the adducts being made up of 8.7% 1:1 adduct, 17.9% 2:1 adduct and 37.5% 3:1 adduct.

Repetition with 117.8 mg (0.38 mmol) $P(OC_6H_5)_3$ produced a total adduct yield of 59.2% for an adduct distribution similar to that obtained with $P(C_6H_5)_3$.

No. 12

Method 8 was repeated with various catalysts instead of the catalyst described there. The quantities of catalyst used (0.38 mmol in each case), the type of catalyst used and the adduct yields (based in each case on conjuene ester) are shown below:

| Catalyst | Adduct yield |
| --- | --- |
| 123.5 mg $Rh(NO_3)_3.2H_2O$ | 17.6% |
| 90.8 mg (0.19 mmol) $[Rh(OAc)_2].2H_2O$ | 46.6% |
| 161.1 mg $Rh(acac)_3$ + 2.0 µl $H_2O$ | 44.1% |
| 151.4 mg $Ru(acac)_3$ + 2.0 µl $H_2O$ | 17.3% |
| 67.4 mg $PdCl_2$ | 14.8% |
| 101.1 mg $PtCl_2$ | 32.3% |
| 113.5 mg $IrCl_3$ + 2.0 µl $H_2O$ | 13.6% |
| 112.7 mg $OsCl_3$ + 2.0 µl $H_2O$ | 20.3% |

Only 1:1 adducts were formed.

No. 13

A $C_{36}$ Guerbet ester of a technical $C_{18}$:2 conjuene fatty acid (17.5 g) having the same composition as for method 1 was reacted with ethylene under the same conditions in the presence of 100 mg $RhCl_3.3H_2O$ and 10 ml hexane. The total adduct yield was 52.4%, based on conjuene ester, the adducts being made of 16.4% 1:1 adduct, 27.0% 2:1 adduct and 9.2% 3:1 adduct.

EXAMPLE 1

A starting material produced by method no. 1 was completely hydrogenated at 70° C./10 bar hydrogen pressure in the presence of 1 mol-%, based on palladium, of a catalyst containing 5% by weight palladium on active carbon. Apart from the hydrogenated adducts and the impurities already present in the starting material, the hydrogenated reaction mixture contained only stearic acid. The hydrogenated addition products were obtained in highly pure form by distillation.

EXAMPLE 2

A starting material produced by method no. 2 was hydrogenated as described in Example 1. The desired mixture of hydrogenated adducts of analogous composition was obtained.

EXAMPLE 3

A product predominantly containing 1:1 adducts of ethylene with $C_{18}$:2 conjuene methyl ester was hydrogenated as described in Example 1. The hydrogenated 1:1 adduct was obtained in highly pure form (approx. 98%, as determined by gas chromatography) from the reaction mixture by molecular distillation. The water-clear, colorless distillate had a particularly low pour point of −58° C. This pour point is considerably lower than, for example, that of isostearic acid methyl ester (approx. −15° C.)

What is claimed is:

1. A process for producing saturated, branched $C_{20-28}$ fatty acids or esters thereof esterified with $C_{1-36}$ alkanols comprising: (a) reacting at least one unsaturated fatty acid containing 18 to 22 carbon atoms and more than one olefinic bond or an ester thereof esterified with a $C_{1-36}$ alkanol with ethylene at a temperature of from about 50° C. to about 140° C. and at a pressure of from about 5 to about 40 bar in the presence of a catalyst consisting essentially of at least one transition metal compound selected from the group consisting of Ru, Rh, Pd, Ir, and Pt, and optionally a phosphine or phosphite ligand and/or an inorganic promoter, wherein the molar ratio of ethylene fatty acid or fatty acid ester is from about 1:1 to about 3:1 to form at least one olefinically unsaturated adduct and, (2) hydrogenating said at least one adduct in the presence of a hydrogenation catalyst at a temperature of from about 70° C. to about 120° C. and under a hydrogen pressure of from 10 to about 30 bar.

2. The process of claim 1 wherein the at least one saturated, branched $C_{18-22}$ fatty acid or ester is a technical mixture of fatty acids or esters containing at least one fatty acid or fatty acid moiety selected from the group consisting of linoleic acid, isomerized linoleic acid containing conjugated double bonds, linolenic acid, arachidonic acid, docosadienoic acid, and eicosapentaenoic acid.

* * * * *

UNITED STATES PATENT AND TRADEMARK OFFICE
CERTIFICATE OF CORRECTION

PATENT NO. : 5,481,025
DATED : Jan. 2, 1996
INVENTOR(S) : Laufenberg et al.

It is certified that error appears in the above-indentified patent and that said Letters Patent is hereby corrected as shown below:

In Col 1, line 36, "Dieis" should read --Diels--.
In Col 1, line 53, "of." should read --cf.--.
In Col 3, line 19, "P(C$_4$H$_g$)$_3$" should read --P(C$_4$H$_9$)$_3$--.
In Col 3, line 20, "P(OC$_4$H$_g$)$_3$" should read --P(OC$_4$H$_9$)$_3$--.
In Col 5, line 42, "P(C$_4$H$_g$)$_3$" should read --P(C$_4$H$_9$)$_3$--.

Signed and Sealed this

Seventh Day of April, 1998

Attest:

Attesting Officer

BRUCE LEHMAN

Commissioner of Patents and Trademarks